(12) United States Patent
Kang et al.

(10) Patent No.: US 8,728,782 B2
(45) Date of Patent: May 20, 2014

(54) METHOD OF EXTRACTING BUTYRIC ACID FROM A FERMENTED LIQUID AND CHEMICALLY CONVERTING BUTYRIC ACID INTO BIOFUEL

(75) Inventors: Sin Young Kang, Daejeon (KR); Cher Hee Park, Incheon (KR); Young Seek Yoon, Gwangju (KR); In Ho Cho, Seoul (KR); Hyung Woong Ahn, Yongin-si (KR); Sam Ryong Park, Daejeon (KR); Jong Hee Song, Daejeon (KR); Seong Ho Lee, Daejeon (KR); Byoung In Sang, Seoul (KR); Young Woong Suh, Seoul (KR); Young Soon Um, Seoul (KR); Sun Mi Lee, Seoul (KR)

(73) Assignees: SK Innovation Co., Ltd., Seoul (KR); Korea Institute of Science and Technology, Seoul (KR)

( * ) Notice: Subject to any disclaimer, the term of this patent is extended or adjusted under 35 U.S.C. 154(b) by 719 days.

(21) Appl. No.: 12/935,075

(22) PCT Filed: Mar. 27, 2009

(86) PCT No.: PCT/KR2009/001580
§ 371 (c)(1),
(2), (4) Date: Aug. 18, 2011

(87) PCT Pub. No.: WO2009/120042
PCT Pub. Date: Oct. 1, 2009

(65) Prior Publication Data
US 2011/0294176 A1    Dec. 1, 2011

(30) Foreign Application Priority Data

Mar. 28, 2008 (KR) .......... 10-2008-0029034
Mar. 10, 2009 (KR) .......... 10-2009-0020368

(51) Int. Cl.
*C12P 7/16* (2006.01)
*C12P 1/00* (2006.01)
*C12P 1/04* (2006.01)

(52) U.S. Cl.
CPC ..................... *C12P 7/16* (2013.01)
USPC ............... 435/160; 435/41; 435/170

(58) Field of Classification Search
CPC combination set(s) only.
See application file for complete search history.

(56) References Cited

U.S. PATENT DOCUMENTS

| 4,260,836 A | 4/1981 | Levy |
| 4,405,717 A | 9/1983 | Urbas |
| 5,753,474 A | 5/1998 | Ramey |
| 2005/0089979 A1* | 4/2005 | Ezeji et al. .................... 435/150 |
| 2008/0015395 A1* | 1/2008 | D'amore et al. ............. 568/697 |
| 2008/0248540 A1* | 10/2008 | Yang ............................. 435/160 |

OTHER PUBLICATIONS

Zetang Wu et al.; "Extractive Fermentation for Butyric Acid Production From Glucose by *Clostridium tyrobutyricum*"; Biotechnology and Bioengineering; Apr. 2003; vol. 82(1); pp. 93-102.

S.R. Roffler et al.; "In Situ Extractive Fermentation of Acetone and Butanol"; Biotechnology and Bioengineering; vol. 31; pp. 135-143 (1988).

\* cited by examiner

*Primary Examiner* — Chris R Tate
*Assistant Examiner* — Douglas F White
(74) *Attorney, Agent, or Firm* — Abelman, Frayne & Schwab

(57) ABSTRACT

Disclosed is a method of converting butyric acid contained in a fermentation broth into biofuel. This chemical conversion method includes separating biohydrogen from gases generated in the course of production of butyric acid through fermentation of carbohydrate, extracting butyric acid from the broth using an insoluble solvent, esterifying butyric acid thus producing butylbutyrate, and hydrogenolyzing all or part of butylbutyrate, thus obtaining butanol. Thereby, biobutanol can be efficiently and economically produced, and butylbutyrate, which has oxidation stability superior to that of conventional biodiesel (fatty acid methyl ester) and is thus regarded as novel biofuel, can be produced together.

15 Claims, 7 Drawing Sheets

ABC fermentation 2-step butanol fermentation

| BED-1 | AD (180s) | DPE (20s) | DP(8s) | | PG (180s) | PPE (20s) | BF (4s) | FP (4s) |
|---|---|---|---|---|---|---|---|---|
| BED-2 | PG (180s) | PPE (20s) | BF (4s) | FP (4s) | AD (180s) | DPE (20s) | DP(8s) | |

AD : adsorption
DPE : depressurizing equalization
DP : depressurization
PG : purge
PPE : pressurizing equalization
BF : backfill
FP : feed pressurization

METHOD OF EXTRACTING BUTYRIC ACID FROM A FERMENTED LIQUID AND CHEMICALLY CONVERTING BUTYRIC ACID INTO BIOFUEL

TECHNICAL FIELD

The present invention relates to a method of converting butyric acid contained in a carbohydrate broth into butanol or butylbutyrate, and more particularly, to a chemical conversion method, which includes separating biohydrogen from gases generated in the course of production of butyric acid through fermentation of carbohydrate, extracting butyric acid from a fermentation broth using an insoluble solvent, esterifying butyric acid thus producing butylbutyrate, and hydrogenolyzing all or part of butylbutyrate, thus obtaining butanol.

BACKGROUND ART

Recently, thorough research, development and businesses for producing bioethanol fuel are being introduced. However, the major problem of bioethanol which is a gasoline blending stock is that, when water is introduced to ethanol-mixed gasoline, it is dissolved into the mixed gasoline, thus water-ethanol mixture is separated from gasoline.

Compared to such ethanol, butanol-mixed gasoline does not absorb water even when water is introduced thereto, and thus, separation of butanol does not occur. Accordingly, the butanol-mixed gasoline does not require the use of additional devices in its storage, transport, supply systems and in vehicles in which it can be used, unlike ethanol-mixed gasoline.

In addition, butanol is advantageous because it has lower vapor pressure than ethanol, thus reducing a probability of causing vapor lock in an automobile engine. Also, unlike ethanol, butanol has an air to fuel ratio similar to that of gasoline, which implies a relatively larger amount of butanol may be mixed with gasoline in a range that does not affect engine performance.

As is apparent from Table 1 below, however, butanol is disadvantageous because it has an octane number approximately equal to that of gasoline, and thus is difficult to use as an octane number booster such as ethanol, MTBE or ETBE.

TABLE 1

|  | Ethanol | Butanol | Gasoline |
|---|---|---|---|
| Solubility in Water | Miscible | 9.1 cc/100 cc | Insoluble |
| Molecular Weight | 46 | 74 | — |
| Molecular Formula | $C_2H_5OH$ | $C_4H_9OH$ | $C_4$~$C_{12}$ |
| Density @20° C., g/cm$^3$ | 0.79 | 0.81 | 0.72 |
| Boiling Point, ° C. | 78 | 117 | 32~210 |
| Flash Point, ° C. | 12 | 35 | −20 |
| Heat Value, Kcal/L | 5,075 | 6,404 | 7,700 |
| Evaporation Heat, Kcal/kg | 200 | 142 | 86 |
| Sensible Heat, Kcal/kg ° C. | 0.62 | 0.56 | 0.5 |
| Air to Fuel Ratio | 9.0 | 11.2 | 14.6 |
| Blending Octane Number | 120 | 90~100 | 91~99 |
| MON (Motor Octane Number) | 96 | 78 | 81~89 |
| Vapor Pressure @100 F., psi | 2 | 0.33 | — |

Despite the above advantages, the reason why biobutanol is not used as fuel is the high production price.

Because butanol is more toxic to organisms than ethanol, it cannot be accumulated to a sufficiently high concentration in a fermentation broth. In the case of typical ABE (Acetone-Butanol-Ethanol) fermentation (FIG. 1) using *Chlostridium acetobutyricum*, productivity of ABE is very low to the level of 0.2 g/h-L, and the maximum concentration of butanol in the fermentation broth is no more than about 1.3%, and thus a fermentation reactor should have a larger capacity relative to a production amount. In particular, the quantity of energy necessary for separation and concentration of butanol from the broth is very large, and thus the production price of biobutanol is considerably higher compared to bioethanol. Also, the strain for producing butanol undesirably loses its butanol production function from a certain point of time due to the toxicity of butanol.

EEI (Energy Environment Inc.), USA, reported a more efficient two-step fermentation process composed of producing only butyric acid using *Clostridium tyrobutylicum* as a strain and then selectively producing only butanol using *Clostridium acetobutylicum* as a strain (U.S. Pat. No. 5,753, 474) (FIG. 1). As such, the productivity may be increased to 6 g/h-L using a fermentation reactor in which the strain is immobilized on a fibrous bed, but the maximum concentration of butanol in the broth is no more than about 2%.

In the case when biobutanol contained in the broth is distilled and recovered, as shown in FIG. 2, separation of 1 l of butanol consumes 5,000 kcal or more of energy and is thus very non-economical in consideration of the combustion heat of butanol being 6,400 kcal/l. Also, EEI proposes gas stripping as a method of recovering butanol present at a low concentration in a fermentation broth. However, compared to typical distillation, gas stripping is unfavorable in terms of energy costs.

Compared to bioethanol, in order to generate economic benefits, biobutanol requires improvement of a butanol fermentation strain for increasing the concentration of butanol in the broth and development of a separation technique for greatly decreasing the separation cost of butanol from the broth at a low concentration.

To reduce the separation cost of butanol from the broth, there is proposed a liquid-liquid extraction method, including recovering butanol from a fermentation broth using a specific solvent having a high butanol extraction coefficient and then recycling the solvent while recovering butanol using the difference in boiling point between the solvent and the butanol.

U.S. Pat. No. 4,260,836 discloses a liquid-liquid extraction method using a fermentation broth containing fluorocarbon having a high butanol extraction coefficient, and U.S. Pat. No. 4,628,116 discloses a liquid-liquid extraction method including liquid-liquid extraction of butanol and butyric acid from a fermentation broth using a vinyl bromide solution.

In Situ Extractive Fermentation of Acetone and Butanol (Biotech. and Bioeng., Vol. 31, P. 135-143, 1988) discloses a liquid-liquid extraction method of butanol using oleyl alcohol.

However, these liquid-liquid extraction methods are not commercially used This is considered to be because solvent extraction of low concentration biobutanol contained in the fermentation broth is still non-efficient.

Because the concentration of butanol in the fermentation broth is very low (less than 2%), even when the above extraction method is employed, there still occur problems in which the cost for separation and purification is excessively high and the strain for producing butanol loses a butanol production function. In order to solve these problems, the strain for producing butanol needs to be improved, but it is difficult to expect drastic improvement of the strain within a short time in consideration of the strain development rate to date.

In accordance with Extractive Fermentation for Butyric Acid Production from Glucose by *Clostridium tyrobutylicum* (Biotech. and Bioeng., Vol. 82, No. 1, P. 93-102, April 2003), as shown in FIG. 3, a fermentation broth discharged from a fibrous bed reactor is transferred to a hollow fiber membrane extraction column As such, in the extraction column, trialkylamine insoluble in water, for example, Alamine 336 is used as an extractant, and butyric acid is combined with trialkylamine and is thus converted into trialkylammonium butyrate and extracted. This extraction process is referred to as reactive extraction. Then, trialkylammonium butyrate is transferred to another hollow fiber membrane extraction column using sodium hydroxide as an extractant. In this extraction column, trialkylamine is recycled, and an aqueous sodium butyrate solution having a high concentration is obtained. When hydrochloric acid is added to the aqueous sodium butyrate solution, an aqueous butyric acid solution may be obtained. This process produces highly pure butyric acid but undesirably consumes 1 mol caustic soda and 1 mol hydrochloric acid to produce 1 mol butyric acid.

U.S. Pat. No. 4,405,717 discloses recovery of acetic acid including treating calcium acetate contained in a fermentation broth with trialkylamine carbonate to thus produce trialkylammonium acetate and calcium carbonate, concentrating the trialkylammonium acetate, and heating the trialkylammonium acetate thus obtaining acetic acid and trialkylamine.

Also, hydrogenation for converting carboxylic acid into corresponding alcohol using a chemical reaction is well known in petrochemical fields.

DISCLOSURE

Technical Problem

However, the reaction for directly hydrogenating butyric acid to produce butanol is problematic in that extreme conditions including high pressure of tens of atm or more are required and a catalyst used there is quickly inactivated, which undesirably makes it difficult to sufficiently ensure life of the catalyst. Hence, in order to sufficiently ensure life of the catalyst while a high yield is maintained under more mild reaction conditions, a method of producing butanol including conversion of butyric acid into butylbutyrate through esterification and then hydrogenolysis of butylbutyrate thus obtaining butanol is devised.

Technical Solution

Therefore, the present invention has been made keeping in mind the problems encountered in the related art and provides a method of efficiently and economically producing biobutanol and butylbutyrate, which are next-generation biofuels, through combining extraction of butyric acid and chemical conversion of butyric acid into butanol.

An aspect of the present invention provides a method of producing biofuel from fermented butyric acid, including supplying a fermentation broth containing butyric acid produced through fermentation of carbohydrate to a liquid-liquid extraction column, thus extracting the butyric acid in the form of trialkylammonium butyrate using trialkylamine as an extraction solvent; supplying the extracted trialkylammonium butyrate a distillation column, thus separating the trialkylammonium butyrate into butyric acid and trialkylamine; and supplying the trialkylamine separated from the distillation column to the liquid-liquid extraction column as the extraction solvent, and converting the butyric acid separated from the distillation column into butylbutyrate through esterification with butanol.

The method according to the present invention may further include converting the butylbutyrate into butanol through hydrogenolysis with hydrogen.

In the method, butanol produced as a result of the conversion of butylbutyrate through the hydrogenolysis with hydrogen may be recycled as butanol reacting with butyric acid.

In the method, part of the converted butanol may be obtained as a final product, and the other part thereof may be used for the esterification with the separated butyric acid.

In the method, the fermentation may be performed by continuously adding an aqueous carbohydrate solution to a fermentation reactor packed with a support on which a strain for producing butyric acid is immobilized so that the aqueous carbohydrate solution is fermented into butyric acid.

In the method, biogas discharged through the fermentation may be supplied to a pressure swing adsorption unit so that the biogas is separated into hydrogen and carbon dioxide, and the separated hydrogen may be used for the hydrogenolysis.

In the method, the pressure swing adsorption unit may include a dewatering pretreatment adsorption column using a silica, alumina or carbonaceous adsorbent and two or more adsorption columns packed with an adsorbent in multiple layers which is composed of one or a mixture of two or more selected from among zeolite A, zeolite X, zeolite Y and carbonaceous adsorbents.

In the method, the trialkylamine may be selected from the group consisting of tripentylamine, trihexylamine, trioctylamine and tridecylamine.

In the method, the esterification of the butyric acid may be performed under reaction conditions including a reaction temperature of 80~300° C., a reaction pressure ranging from atmospheric pressure to 20 atm, a space velocity of 0.1~5.0 $h^{-1}$ and a molar ratio of butanol to butyric acid of 1~10, in the presence of at least one catalyst having an esterification function.

In the method, the esterification of the butyric acid may be performed under reaction conditions including the reaction temperature of 90~200° C., the reaction pressure ranging from atmospheric pressure to 10 atm, the space velocity of 0.3~2.0 $h^{-1}$ and the molar ratio of butanol to butyric acid of 1.5~5.

In the method, the catalyst used for the esterification of the butyric acid may be a homogeneous catalyst or a heterogeneous catalyst, in which the homogeneous catalyst may include sulfuric acid, hydrochloric acid or nitric acid, and the heterogeneous catalyst may be selected from the group consisting of solid acid catalysts having super strong acid properties, including an ion exchange resin, zeolite, silica alumina, alumina, sulfonated carbon and heteropolyacid.

In the method, the hydrogenolysis may be performed under reaction conditions including a reaction temperature of 120~300° C., a reaction pressure ranging from atmospheric pressure to 100 atm, a space velocity of 0.1~5.0 $h^{-1}$ and a molar ratio of hydrogen to butylbutyrate of 1~100, in the presence of a catalyst having a hydrogenation function in a form in which at least one metal or metal oxide is supported on a support.

In the method, the hydrogenolysis may be performed under reaction conditions including the reaction temperature of 150~250° C., the reaction pressure of 5~50 atm, the space velocity of 0.3~2.0 $h^{-1}$ and the molar ratio of hydrogen to butylbutyrate of 10~50.

In the method, the metal or metal oxide may be selected from the group consisting of copper, zinc, chromium, nickel, cobalt, molybdenum, tungsten, oxides thereof, platinum, palladium, ruthenium, rubidium and oxides thereof.

In the method, the biofuel may be butanol, butylbutyrate or a mixture of butanol and butylbutyrate.

Advantageous Effects the present invention has been made keeping in mind the problems encountered in the related art and provides a method of efficiently and economically producing biobutanol and butylbutyrate, which are next-generation biofuels, through combining extraction of butyric acid and chemical conversion of butyric acid into butanol.

BEST MODE

Hereinafter, a detailed description will be given of the embodiments of the present invention, with reference to the appended drawings.

The present invention pertains to a method of converting butyric acid contained in a fermentation broth into biofuel. In the present invention, the biofuel includes biobutanol, butylbutyrate or a mixture of biobutanol and butylbutyrate.

Figure 1:
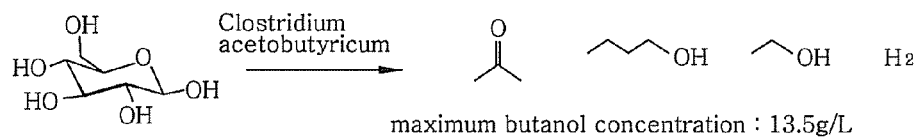
FIG. 1 shows reaction schemes of a conventional fermentation technique for producing butanol.
Figure 1:
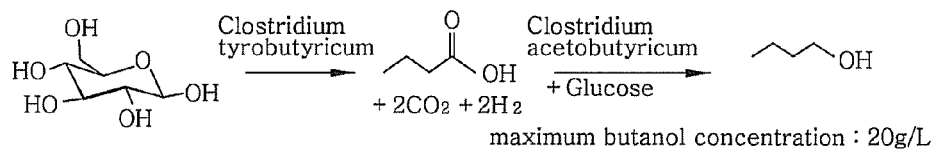
Figure 2:
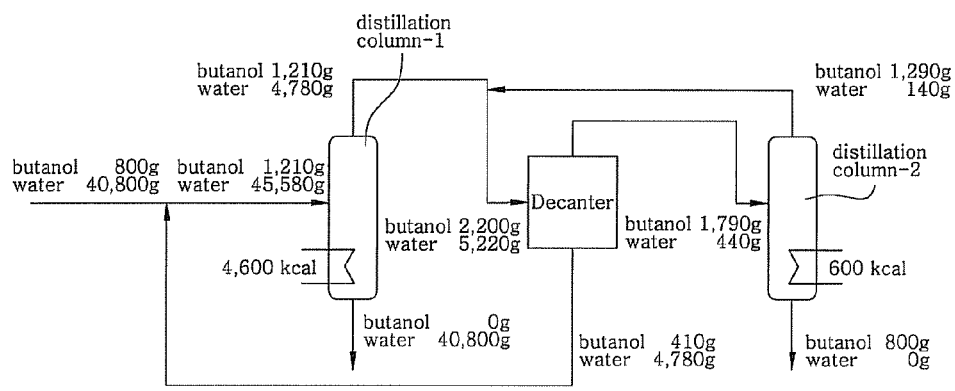
FIG. 2 shows distillation and recovery of biobutanol contained in a fermentation broth, including materials and energy vales at respective steps.
Figure 3:
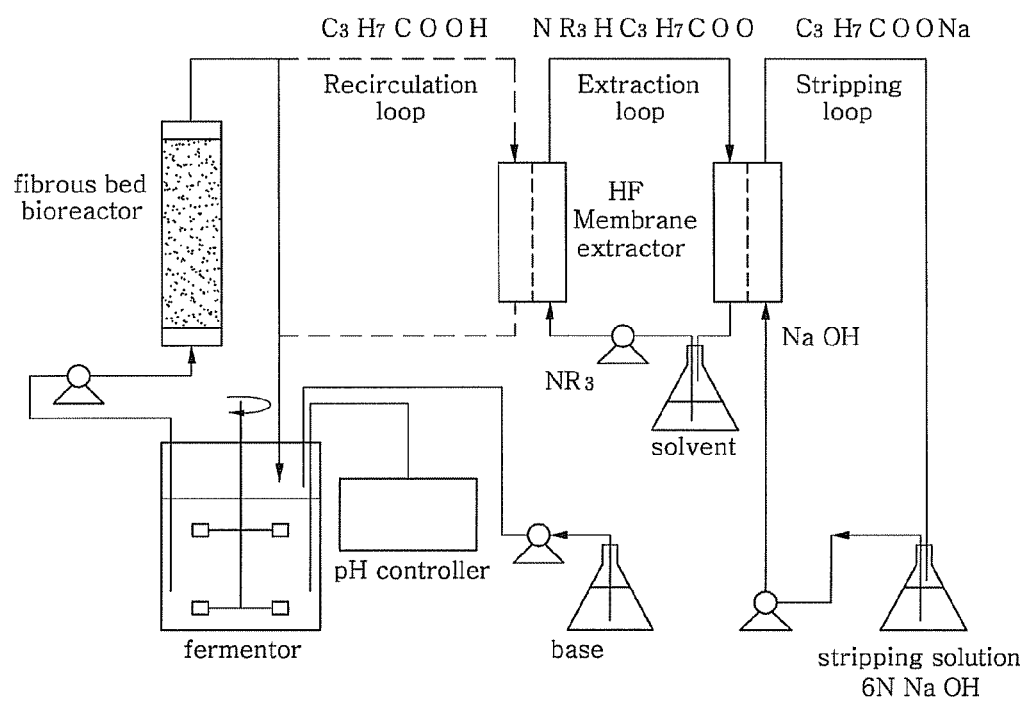
FIG. 3 schematically shows an experimental apparatus for extractive fermentation of butyric acid according to a conventional technique.
Figure 4:
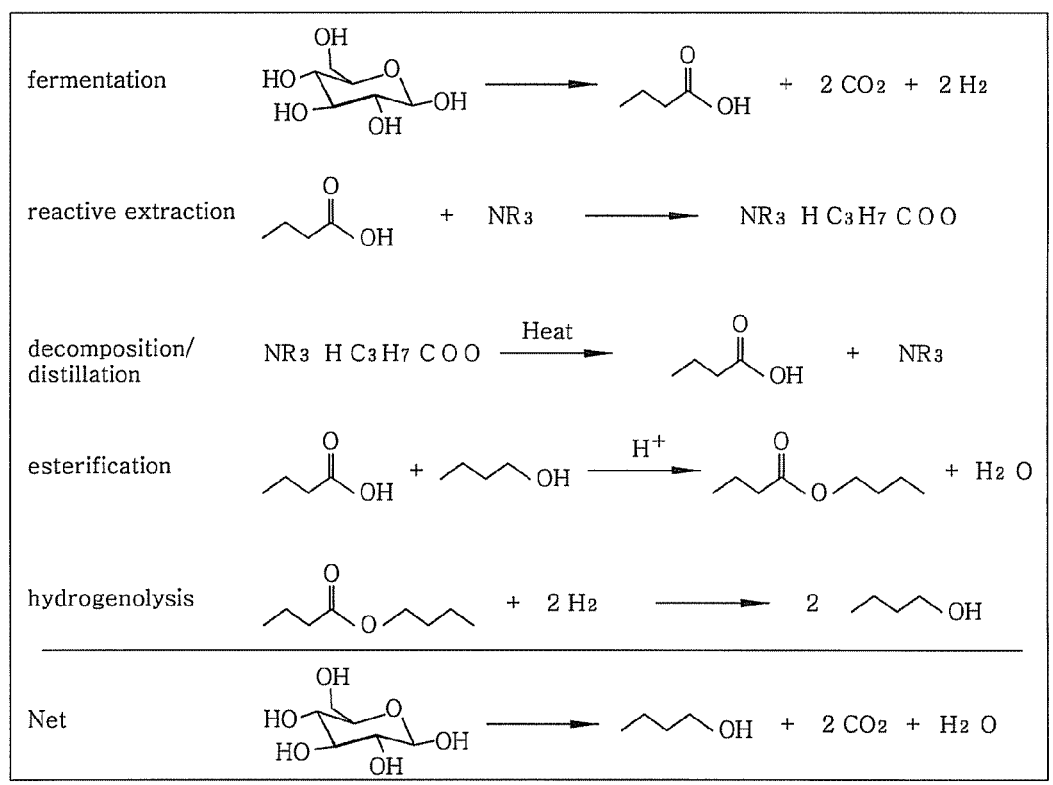
FIGS. 4 and 5 show extractive fermentation, esterification and hydrogenolysis of butyric acid according to the present invention.
Figure 5:
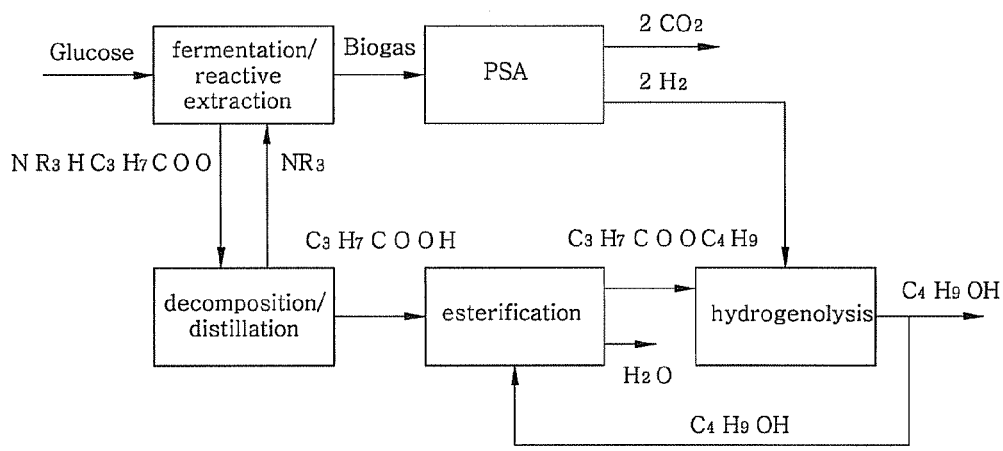
Figure 6:
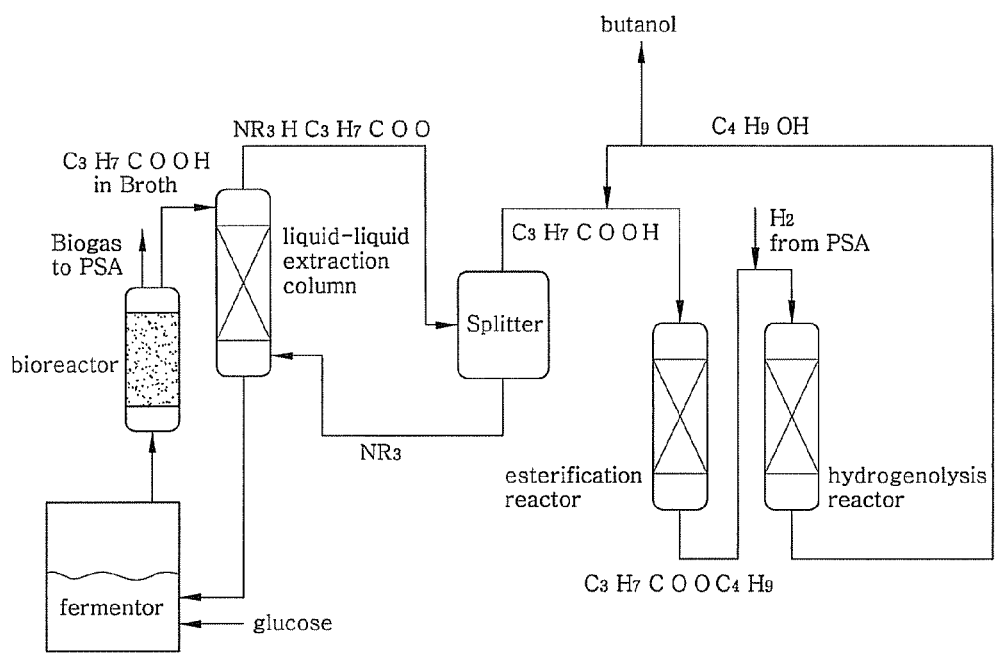
FIG. 6 shows a process of producing biobutanol according to the present invention.

As shown in FIGS. 4 to 6, the preparation of butanol according to the present invention largely includes extractive fermentation, esterification, and hydrogenolysis, in which the extractive extraction includes fermentation, reactive extraction, and decomposition/distillation. In the present invention, hydrogen gas produced in the course of fermentation may be used for hydrogenolysis, and part of butanol obtained in the course of hydrogenolysis may be used for esterification, thereby maximizing preparation efficiency.

In the present invention, a fermentation reactor is packed with a support on which a strain for producing butyric acid is immobilized, and an aqueous carbohydrate solution is continuously added thereto so that it is fermented into butyric acid.

The carbohydrate used for fermentation into butyric acid includes glucose or sugarcane juice. Alternatively, a pentose-hexose mixture obtained through hydrolysis of wood biomass may be used.

Examples of the strain for producing butyric acid through fermentation of the aqueous carbohydrate solution include *Clostridium tyrobutylicum*, *Clostridium butylicum*, and *Clostridium acetobutyricum*.

The strain for producing butyric acid is provided in the form of being immobilized on the support in the reactor, and the support for immobilizing the strain includes a porous polymer support composed of polyurethane, in consideration of immobilization stability.

In the case where carbohydrate is fermented using a strain such as *Clostridium tyrobutylicum*, not only butyric acid but also biogas such as carbon dioxide and hydrogen are produced. The biogas produced in the course of butyric acid fermentation is composed of hydrogen and carbon dioxide at a volume ratio of about 1:1, and contains water of about 30 $g/m^3$ corresponding to saturated water vapor pressure at a fermentation temperature of 30° C.

The biogas obtained from the fermentation reactor is supplied to a pressure swing adsorption (PSA) unit so that it is separated into hydrogen and carbon dioxide. Depending on needs, a dewatering pretreatment adsorption column (water trap) may be disposed upstream of the PSA unit, thereby primarily removing water.

The gas mixture of hydrogen and carbon dioxide may be easily separated upon both adsorption and membrane separation. As such, compared to membrane separation requiring a large-scale membrane module, PSA which is able to reduce investment cost is more advantageous in terms of cost.

Figure 9:
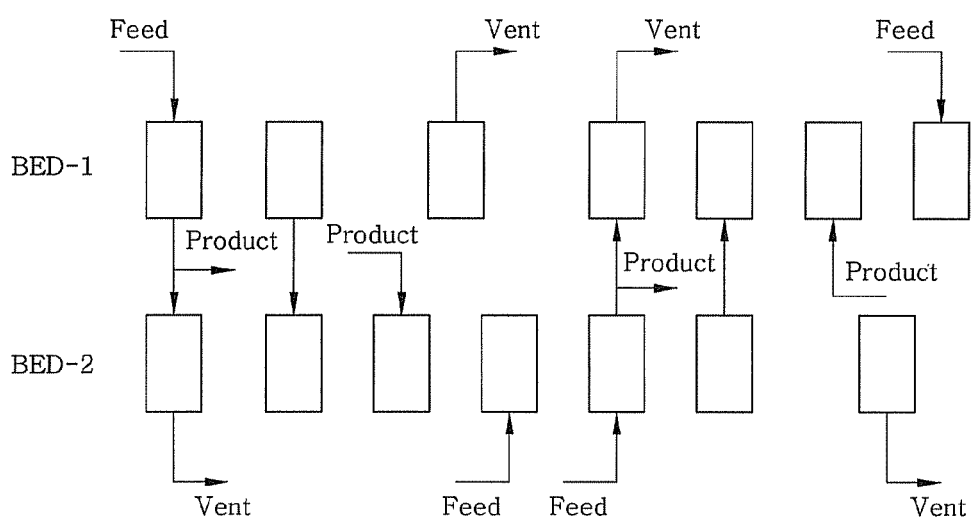
FIG. 9 shows operation of the pressure swing adsorption unit used in the present invention.

The operation of the PSA unit used in the present invention is shown in FIG. 9. The PSA unit used for the method according to the present invention includes a water trap using a silica, alumina or carbonaceous adsorbent and two or more adsorption columns packed with an adsorbent in multiple layers which is composed of one or a mixture of two or more selected from among zeolite A, zeolite X, zeolite Y and carbonaceous adsorbents. The operation pressure may be 2~15 atm and in particular 5~12 atm upon adsorption, and may be atmospheric pressure upon desorption. The PSA unit is operated at room temperature.

In the present invention, the PSA unit for adsorption and separation of a hydrogen/carbon dioxide/water gas mixture is operated at about 10 atm. In this case, the resulting hydrogen at 10 atm may be used for hydrogenolysis which will be mentioned later, without additional application of pressure.

Further, the fermentation broth containing butyric acid produced through fermentation is transferred to a liquid-liquid extraction column for separation of butyric acid. In the liquid-liquid extraction column, trialkylamine insoluble in water is used as an extraction solvent, and thus butyric acid is reacted with trialkylamine so that it is converted into trialkylammonium butyrate and thus extracted.

As such, examples of trialkylamine used as the extraction solvent include tripentylamine, trihexylamine, trioctylamine and tridecylamine, which are insoluble in water. Because mono-amine or di-amine may produce amide in the course of extraction and recovery, it is not applied to the method according to the present invention.

The extract passed through the liquid-liquid extraction column is composed of trialkylamine used as the extraction solvent and trialkylammonium butyrate converted from butyric acid, which are mixed together. When this extract is supplied to a downstream distillation column, trialkylammonium butyrate is decomposed into butyric acid and trialkylamine, thus recovering butyric acid from the top of the distillation column and trialkylamine from the bottom of the distillation column The operation temperature of the distillation column may slightly vary depending on the type of trialkylamine used as the extraction solvent. In the case of tripentylammonium butyrate produced using tripentylamine as the extraction solvent, decomposition begins at 90~100° C. As such, trialkylamine recovered from the bottom of the distillation column may be reused by being supplied to the liquid-liquid extraction column as the extraction solvent for liquid-liquid extraction of butyric acid as mentioned above.

In order to increase separation efficiency upon liquid-liquid extraction of butyric acid, a mixture of trialkylamine and a co-solvent such as diisopropylketone may be used as the extraction solvent.

A reaction for producing butanol through direct hydrogenation of butyric acid separated from the top of the distillation column is disadvantageous because extreme reaction conditions including high pressure of tens of atm or more are required and a catalyst used there is quickly inactivated, which undesirably makes it difficult to sufficiently ensure life of the catalyst. Thus, in the present invention, to sufficiently ensure life of the catalyst while maintaining a high yield under more mild reaction conditions, a method of producing butanol including esterifying butyric acid thus obtaining butylbutyrate and then hydrogenolyzing butylbutyrate thus producing butanol is applied.

In the present invention, butyric acid separated from the top of the distillation column is supplied to an esterification reactor along with butanol and thus converted into butylbutyrate. In this case, butanol used for the esterification may include part of butanol produced through hydrogenolysis which will be described later.

The esterification may be performed in the presence of at least one catalyst having an esterification function, under conditions including a reaction temperature of 80~300° C., a reaction pressure ranging from atmospheric pressure to 20 atm, a space velocity of 0.1~5.0 $h^{-1}$ and a molar ratio of butanol to butyric acid of 1~10, and in particular, under conditions including a reaction temperature of 90~200° C., a reaction pressure ranging from atmospheric pressure to 10 atm, a space velocity of 0.3~2.0 $h^{-1}$ and a molar ratio of butanol to butyric acid of 1.5~5.

If the reaction temperature is lower than 80° C., catalytic activity is low, undesirably to decreasing conversion. In contrast, if the reaction temperature is higher than 300° C., by-products may be formed in a larger amount, undesirably decreasing selectivity. The reaction pressure is maintained as low as possible, so that part of a feed is evaporated to thus cause a reaction in a gas-liquid coexisting state in the presence of the catalyst, resulting in an increased thermodynamic equilibrium conversion.

As the space velocity is lowered, conversion is increased and the selectivity is decreased. However, in order to decrease the size of the reactor or increase the productivity, there is a need to increase the space velocity as much as possible.

The esterification allows butanol and butyric acid to react at a molar ratio of 1:1 thus producing 1 mol of butylbutyrate and 1 of mol water. However, butanol should be excessively supplied to increase the conversion of butyric acid. As the ratio of butanol to butyric acid approximates a stoichiometric ratio, the conversion of butyric acid decreases to the level of 70~80%. In the case where the molar ratio of butanol to butyric acid is 2 or more, conversion of 95% or more may be obtained. However, if the molar ratio is too high, the production of by-products is increased, and thus the selectivity may be decreased.

Because part of the feed begins to be evaporated at the reaction temperature to thus cause a reaction in a gas-liquid coexisting state, the feed may be supplied from the bottom of the reactor to the top thereof so as to prevent a channeling phenomenon and facilitate contact with the catalyst. However, when the reactor is configured such that that the feed is prevented from channeling and is brought into efficient contact with the catalyst bed to thus attain uniform catalytic activity, there is no essential need to supply the feed from the bottom of the reactor to the top thereof.

The catalyst for esterification may be a homogeneous or heterogeneous catalyst Examples of the homogeneous catalyst include homogeneous acid catalysts, such as sulfuric acid, hydrochloric acid and nitric acid, and the heterogeneous catalyst may be selected from the group consisting of solid acid catalysts having super strong acid properties, including an ion exchange resin, zeolite, silica alumina, alumina, sulfonated carbon and heteropolyacid.

Part of butylbutyrate produced through the esterification is discharged as a final product, and the other part thereof may be supplied to a downstream hydrogenolysis reactor.

As is apparent from Table 2 below, the octane number of butylbutyrate is equal to that of butanol, and thus butylbutyrate may be used as biofuel for gasoline having high quality along with butanol. Also, the cetane number of butylbutyrate is about 30 and the flash point thereof satisfies a standard for diesel, and thus butylbutyrate is expected to serve as a novel form of biodiesel.

TABLE 2

|  | Butanol | Butylbutyrate | Soybean Biodiesel |
|---|---|---|---|
| Solubility in Water | 9.1 cc/100 cc | Insoluble | Insoluble |
| Molecular Weight | 74 | 144 | $RCOOCH_3$ |
| Molecular Formula | $C_4H_9OH$ | $C_3H_7COOC_4H_9$ |  |
| Density @20° C., g/cm$^3$ | 0.81 | 0.8692 | 0.87~0.89 |
| Boiling Point, ° C. | 117 | 165 | 340~380 |
| Flash Point, ° C. | 35 | 49 | 180~185 |
| Heat Value, Kcal/L | 6,404 | 6,350 | 8,300 |
| Blending Octane Number | 95~100 | 95~100 | — |
| Blending Cetane Number | 0 | 25~30 | 40~45 |

In the case where the amount of hydrogen gas generated through butyric acid fermentation is not sufficient, part of butylbutyrate obtained through esterification is not supplied to the hydrogenolysis reactor but may be discharged as a final product. In this case, the consumption of hydrogen may be decreased to a maximum of 50%.

Also, part of butylbutyrate other than the part of butylbutyrate which is discharged as the final product may be supplied to the downstream hydrogenolysis reactor, and may be converted into butanol through hydrogenolysis.

As the hydrogen gas necessary for hydrogenolysis, particularly useful is hydrogen separated using the PSA unit from the gas produced through the fermentation as mentioned above.

The hydrogenolysis in the hydrogenolysis reactor may be performed using a catalyst having a hydrogenation function in the form in which at least one metal or metal oxide is supported on a support. Examples of the metal or metal oxide supported on the support include copper, zinc, chromium, nickel, cobalt, molybdenum, oxides thereof, precious metals such as platinum, palladium, rhodium and ruthenium, and oxides thereof.

The hydrogenolysis may be performed under conditions including a reaction temperature of 120~300° C. and a reaction pressure ranging from atmospheric pressure to 100 atm, and in particular under conditions including a reaction temperature of 150~250° C. and a reaction pressure of 5~50 atm. Typically, hydrogenation or hydrogenolysis increases the conversion of a reactant and decreases selectivity for a desired product in proportion to an increase in the reaction temperature, and increases the conversion in proportion to an increase in the reaction pressure.

Further, because the conversion of the reactant and the selectivity for the product are affected by the reaction temperature, the reaction pressure, the space velocity for contact efficiency between the reactant and the catalyst, and the ratio of reactants upon use of two or more reactants, the reaction conditions should be optimized in consideration of the effects of these parameters.

When part of the feed is evaporated in the reaction temperature range and the hydrogen gas is supplied together, the reaction occurs in a gas-liquid coexisting state. So, in order to prevent a channeling phenomenon and facilitate contact with the catalyst, the feed is supplied from the bottom of the reactor to the top of the reactor. However, when the reactor is configured such that the feed is prevented from channeling and is brought into efficient contact with the catalyst bed to thus attain uniform catalytic activity, there is no essential need to supply the feed from the bottom of the reactor to the top thereof.

Part of butanol produced through hydrogenolysis is discharged as a final product, and the other part thereof is used for the esterification.

Obtained as final products, butanol and butylbutyrate may be used alone or in a mixture when mixed with gasoline.

MODE FOR INVENTION

A better understanding of the present invention may be obtained through the following examples which are set forth to illustrate, but are not to be construed to limit the present invention.

EXAMPLE 1

Continuous Production of Butyric Acid in Tube type Fermentor Packed with Immobilized Strain An anaerobic reactor for producing butyric acid using glucose as a carbon source and *Clostridium tyrobutylicum* was operated at 37° C. in the presence of a basal medium.

For the high-concentration culture of *Clostridium tyrobutylicum*, the anaerobic reactor in the form of a column packed with a porous polymer support was used. The total volume of the reactor was 2.5 L, and the volume of the packed support was 1.2 L.

As the polymer support, a regular hexagonal porous polymer support composed of polyurethane sponge may be used. While glucose having a concentration of 20 g/L was continuously supplied, the concentration of produced butyric acid was measured.

5 days after *Clostridium tyrobutylicum* was inoculated in the reactor, the concentration of butyric acid was increased to 8~9 g/L. The yield of butyric acid was 0.43 g butyric acid/g glucose, and the production rate of butyric acid was 6.7~7.3 g/L·h.

The concentration of *Clostridium tyrobutylicum* immobilized on the porous polymer support was 70 g/L or more. Even upon continuous operation of 20 days or longer, the detachment of microorganisms was not found, from which *Clostridium tyrobutylicum* could be confirmed to be stably immobilized on the porous polymer support. The butyric acid was stably produced at a concentration of 8 g/L or more.

EXAMPLE 2

Extraction and Distillation of Butyric Acid

Into a 500 cc cylinder, 200 g of water, 44 g of butyric acid, and 150 g of tripentylamine were introduced and sufficiently stirred. After complete layer separation, the amount of butyric acid contained in a water layer was measured. The concentration of butyric acid contained in the water layer was no more than 0.2%. Thus, it could be confirmed that 99% or more of introduced butyric acid was transferred to a tripentylamine layer and mainly combined with tripentylamine and thus converted into tripentylammonium butyrate.

Figure 7:
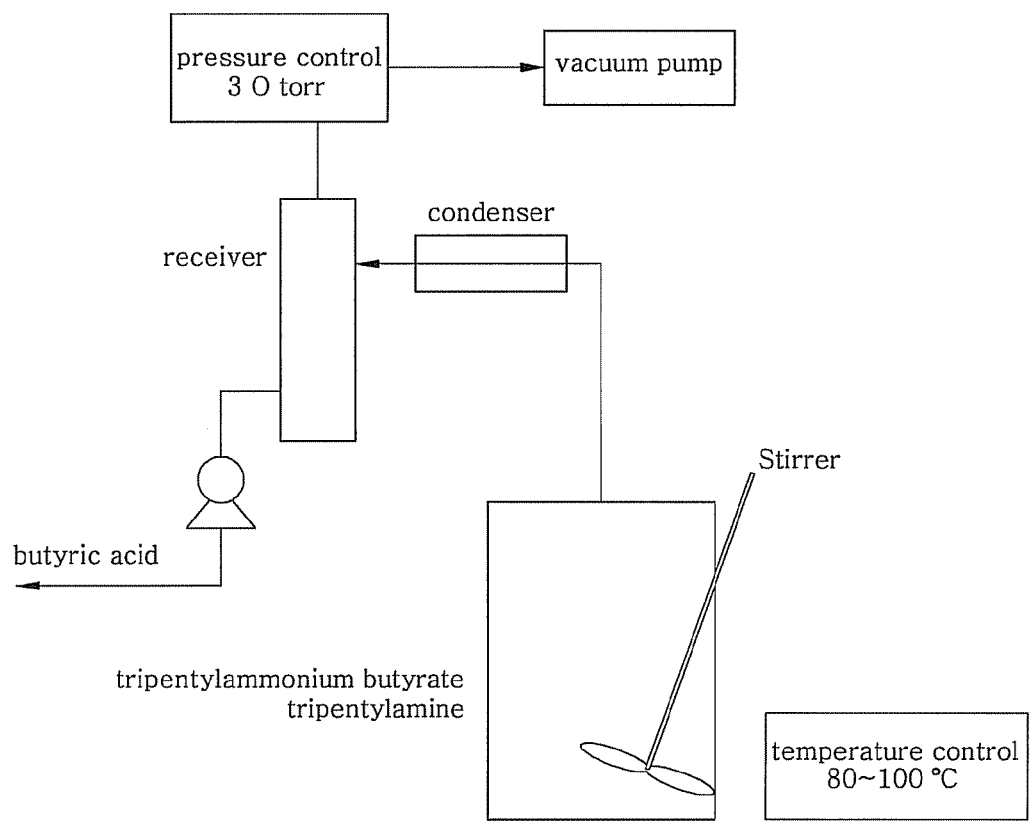
FIG. 7 schematically shows an experimental apparatus for decomposition/distillation of trialkylammonium butyrate used in the present invention.

175 g of the tripentylammonium butyrate layer was recovered from the cylinder, placed in a batch reactor and stirred, as shown in FIG. 7. In a state in which the pressure of the reactor was maintained at 30 torr, the internal temperature of the reactor was gradually increased from 80° C. in intervals of 10° C.

From the point of time at which the internal temperature of the reactor reached 90° C., flow of butyric acid vapor into a condenser was observed. The internal temperature of the reactor was set to 100° C.

The operation of the reactor was stopped at a point of time at which the flow of butyric acid vapor into the condenser was not observed. Thereafter, 35 g of butyric acid was recovered from a receiver.

EXAMPLE 3

Esterification of Butanol and Butyric Acid I

As a strong acid ion exchange resin catalyst, 6 cc of DOWEX 50WX8-400 available from DOW was loaded into a continuous tube type reactor having an inner diameter of 10 mm While nitrogen gas was allowed to flow into the reactor, the temperature of the reactor was increased to 100° C. which was the reaction temperature. A feed in which butanol and butyric acid were mixed at a molar ratio of 2:1 was supplied at a rate of 6 cc/h. Because part of the feed began to be evaporated at the reaction temperature to thus cause a reaction in a gas-liquid coexisting state, the feed was supplied from the bottom of the reactor to the top thereof to prevent a channeling phenomenon and facilitate contact with the catalyst. 4 hours after the feed was supplied at the reaction temperature, a product was taken out of the reactor and was sampled four times at temporal intervals of 6 hours. The product was analyzed using a gas chromatography analyzer [HP5890 series, available from Hewlett Packard Co.] provided with a polyethyleneglycol column (HP-INNOWax column, 50 m×0.2 mm×0.4 mm) and a flame ionization detector (FID). The measured conversion and selectivity values were averaged. While the reaction temperature was increased to 110° C., 120° C. and 130° C., the same procedures as above were performed, thus evaluating the effects of the reaction temperature. The results are summarized in Table 3 below.

TABLE 3

Results of Esterification of Butyric Acid using DOWEX 50WX8-400 Catalyst

| Temp. of Catalyst Bed (° C.) | 100 | 110 | 120 |
|---|---|---|---|
| Conversion of Butyric Acid (%) | 97.3 | 98.3 | 98.2 |
| Selectivity for Butylbutyrate (%) | 99.4 | 97.0 | 93.3 |
| Yield of Butylbutyrate (%) | 96.7 | 95.3 | 91.7 |

EXAMPLES 4~6

Esterification of Butanol and Butyric Acid II

The effects of the catalyst were evaluated in the same manner as in Example 3, with the exception that DOWEX 50WX2-400 available from DOW and Amberlyst 70 and Amberlyst 121 available from ROHM & HAAS were used as strong acid ion exchange resin catalysts. The results are summarized in Tables 4~6 below. The conversion of butyric acid was increased in proportion to an increase in the reaction temperature in the presence of almost all of the catalysts. However, the production of a by-product such as dibutylether was increased, undesirably decreasing selectivity for butylbutyrate.

In the case of DOWEX 50WX8-400 and Amberlyst 70 catalysts, a reaction temperature was set to 100~110° C., and in the case of DOWEX 50WX2-400 and Amberlyst 121 catalysts, the reaction temperature was set to 110~120° C., thus producing butylbutyrate at a maximum yield of 95-96%.

TABLE 4

Results of Esterification of Butyric Acid using DOWEX 50WX2-400 Catalyst

| Temp. of Catalyst Bed (° C.) | 100 | 110 | 120 |
|---|---|---|---|
| Conversion of Butyric Acid (%) | 92.8 | 96.3 | 97.5 |
| Selectivity for Butylbutyrate (%) | 98.6 | 99.2 | 98.9 |
| Yield of Butylbutyrate (%) | 91.4 | 95.5 | 96.4 |

TABLE 5

Results of Esterification of Butyric Acid using Amberlyst 70 Catalyst

| Temp. of Catalyst Bed (° C.) | 100 | 110 | 120 |
|---|---|---|---|
| Conversion of Butyric Acid (%) | 95.7 | 98.2 | 98.3 |
| Selectivity for Butylbutyrate (%) | 99.4 | 98.0 | 95.4 |
| Yield of Butylbutyrate (%) | 95.1 | 96.2 | 93.8 |

TABLE 6

Results of Esterification of Butyric Acid using Amberlyst 121 Catalyst

| Temp. of Catalyst Bed (° C.) | 100 | 110 | 120 |
|---|---|---|---|
| Conversion of Butyric Acid (%) | 93.8 | 96.2 | 97.2 |
| Selectivity for Butylbutyrate (%) | 99.3 | 99.1 | 97.5 |
| Yield of Butylbutyrate (%) | 93.2 | 95.3 | 94.8 |

EXAMPLES 7 AND 8

Esterification of Butanol and Butyric Acid III

The effects of the catalyst were evaluated in the same manner as in Example 3, with the exception that DOWEX 50WX8-400 available from DOW and Amberlyst 70 available from ROHM & HAAS were used as strong acid ion exchange resin catalysts, the space velocity was set to 0.5 h$^{-1}$, and the molar ratio of butanol and butyric acid was set to 3. The results are given in Tables 7 and 8 below.

TABLE 7

Results of Esterification of Butyric Acid using DOWEX 50WX8-400 Catalyst

| Temp. of Catalyst Bed (° C.) | 100 | 110 | 120 |
|---|---|---|---|
| Conversion of Butyric Acid (%) | 97.8 | 98.4 | 98.8 |
| Selectivity for Butylbutyrate (%) | 98.7 | 97.6 | 90.5 |
| Yield of Butylbutyrate (%) | 96.6 | 96.0 | 89.5 |

TABLE 8

Results of Esterification of Butyric Acid using Amberlyst 70 Catalyst

| Temp. of Catalyst Bed (° C.) | 100 | 110 | 120 |
|---|---|---|---|
| Conversion of Butyric Acid (%) | 97.2 | 98.3 | 99.3 |
| Selectivity for Butylbutyrate (%) | 98.1 | 98.5 | 97.0 |
| Yield of Butylbutyrate (%) | 95.3 | 96.8 | 96.3 |

EXAMPLE 9

Esterification of Butanol and Butyric Acid IV

The long durability of the catalyst was evaluated in the same manner as in Example 3, with the exception that Amberlyst 70 available from ROHM & HAAS was used as a strong acidic ion exchange catalyst and hydrolysis was performed at a reaction temperature of 110° C. The results are given in Table 9 below. In a reaction which proceeded continuously for 1 month, the conversion of butyric acid was 99% or more, and the selectivity for butylbutyrate was 97% or more. When the surface of the catalyst was observed before and after the reaction using an electron microscope, the surface of the catalyst after the reaction was seen to be clean without attached impurities. Thus, the activity of the catalyst was ascertained to be maintained for an extended period.

TABLE 9

Results of Durability of Amberlyst 70 Catalyst for Esterification of Butyric Acid

| Reaction Time (days) | 2 | 10 | 20 | 30 |
|---|---|---|---|---|
| Conversion of Butyric Acid (%) | 99.2 | 98.9 | 99.5 | 99.7 |
| Selectivity for Butylbutyrate (%) | 96.0 | 98.1 | 98.3 | 97.5 |
| Yield of Butylbutyrate (%) | 95.2 | 97.0 | 97.8 | 97.2 |

EXAMPLE 10

Recovery of Hydrogen from Hydrogen Gas Mixture as Fermentation By-Product

Figure 8:
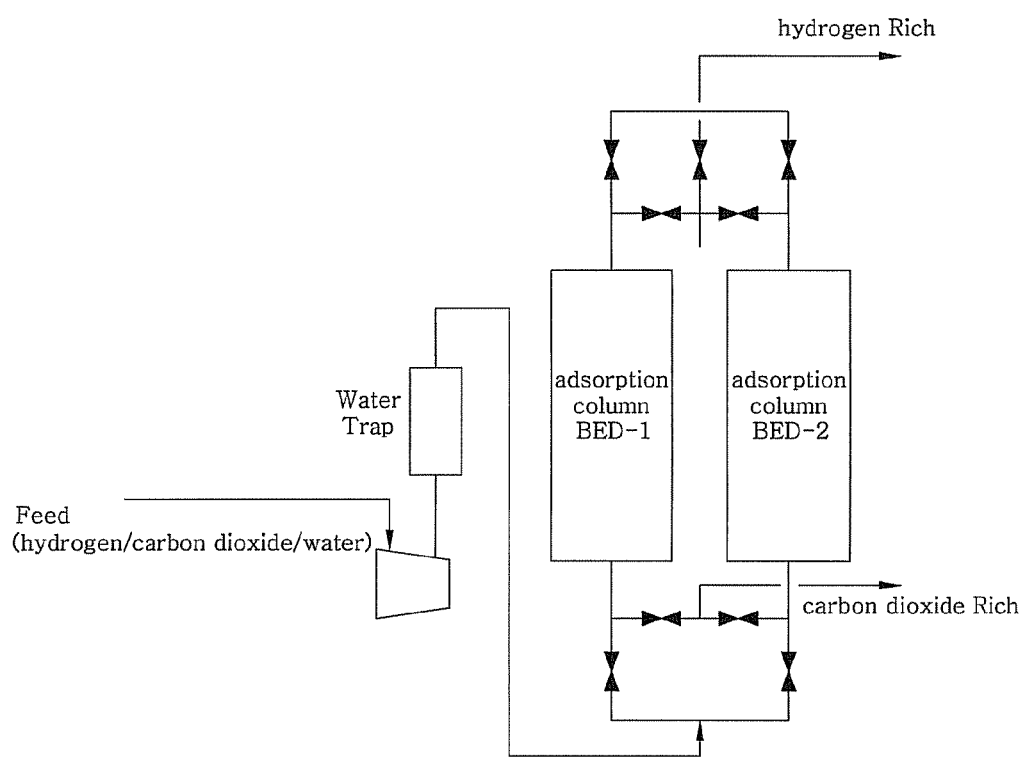
FIG. 8 schematically shows a pressure swing adsorption unit used in the present invention.

The gas mixture of hydrogen and carbon dioxide at a molar ratio of 1:1 was separated using a PSA unit having two adsorption columns packed with a zeolite adsorbent, as shown in FIG. 8.

The operation temperature of the PSA unit was 30° C., and the operation pressure was 10 atm upon adsorption and was atmospheric pressure upon desorption. The specific operation of the PSA unit having two columns is shown in FIG. 9.

Through the operation of the PSA unit having two columns shown in FIG. 9, hydrogen having a purity of 99.9% or more could be obtained, and the total recovery was 83%.

FIG. 9 shows the separation of hydrogen through a sequential 8-step operation using two adsorption columns, in which 'Vent' indicates a carbon dioxide stream and 'Product' indicates a hydrogen stream.

EXAMPLE 11

Hydrogenolysis of Butylbutyrate I

A commercially available catalyst for water gas shift reaction (copper/zinc oxide/gamma alumina, CuO: 51 wt %, ZnO: 31 wt %, alumina: the balance) was incorporated into a palladium nitrate solution through Incipient Wetness, dried at 80° C. for 12 hours and burned at 400° C. for 4 hours, thus preparing a catalyst. The amount of palladium nitrate used was quantitatively set so that the amount of palladium in the prepared catalyst was 1.0 wt %. 12.0 cc of the prepared catalyst was loaded into a continuous tube type reactor having an inner diameter of 10 mm and then subjected to reduction treatment using 5 vol % of a hydrogen-nitrogen gas mixture at 230° C. for 3 hours and then using 20 vol % of a hydrogen-nitrogen gas mixture at 230° C. for 2 hours. Subsequently, butylbutyrate was supplied at a rate of 3.6 cc/h and hydrogen was supplied at a rate of 14.6 L/h. Also, the space velocity was set to 0.3 $h^{-1}$, the molar ratio of hydrogen to butylbutyrate was 30, and the temperature of the catalyst bed was 150° C. Further, the downstream reactor pressure was maintained at 10 atm.

The temperature of the catalyst bed reached the peak, after which a liquid product was sampled four times at temporal intervals of 6 hours. The product was analyzed using a gas chromatography analyzer [HP5890 series, available from Hewlett Packard Co.] with a polyethyleneglycol column (HP-INNOWax column, 50 m×0.2 mm×0.4 mm) and an FID. The measured conversion and selectivity values were averaged. The results are given in Table 6 below.

The temperature of the catalyst bed was changed to 175° C. or 200° C. and thus the same procedures as above were performed. The results are summarized in Table 10 below. As the reaction temperature was increased, the conversion of butylbutyrate was increased and the selectivity was decreased.

TABLE 10

Effects of Reaction Temperature on Hydrogenolysis of Butylbutyrate

| Temp. of Catalyst Bed (° C.) | 150 | 175 | 200 |
|---|---|---|---|
| Conversion of Butylbutyrate (%) | 94.4 | 98.7 | 97.7 |
| Selectivity for Butanol (%) | 99.8 | 99.8 | 99.2 |
| Yield of Butanol (%) | 94.2 | 98.5 | 96.7 |

EXAMPLE 12

Hydrogenolysis of Butylbutyrate II

The effects of the space velocity were evaluated in the same manner as in Example 10, with the exception that the reaction temperature was uniformly maintained at 175° C. and the space velocity was changed to 0.5, 0.7 and 1.0 $h^{-1}$. The results are summarized in Table 11 below. As the space velocity was increased, the conversion of butylbutyrate rapidly decreased.

TABLE 11

Effects of Space Velocity on Hydrogenolysis of Butylbutyrate

| Space Velocity ($h^{-1}$) | 0.3 | 0.5 | 0.7 | 1.0 |
|---|---|---|---|---|
| Conversion of Butylbutyrate (%) | 98.7 | 87.2 | 82.0 | 78.0 |
| Selectivity for Butanol (%) | 99.8 | 99.6 | 99.8 | 99.7 |
| Yield of Butanol (%) | 98.5 | 86.8 | 81.8 | 77.7 |

EXAMPLE 13

Hydrogenolysis of Butylbutyrate III

The effects of the hydrogen to butylbutyrate ratio were evaluated in the same manner as in Example 11, with the exception that the reaction temperature was set to 175° C., the space velocity was maintained at 0.5 $h^{-1}$, and the molar ratio of hydrogen to butylbutyrate was changed to 10, 20, 30 and 35. The results are summarized in Table 12 below. As the hydrogen to butylbutyrate ratio was increased, the conversion of butylbutyrate rapidly increased.

TABLE 12

Effects of Hydrogen to Butylbutyrate Ratio on Hydrogenolysis

| Hydrogen/Butylbutyrate Ratio (mol) | 10 | 20 | 30 | 35 |
|---|---|---|---|---|
| Conversion of Butylbutyrate (%) | 72.7 | 85.5 | 87.2 | 89.4 |
| Selectivity for Butanol (%) | 99.3 | 99.6 | 99.6 | 99.6 |
| Yield of Butanol (%) | 72.2 | 85.2 | 86.8 | 85.8 |

EXAMPLE 14

Hydrogenolysis of Butylbutyrate IV

The long durability of the catalyst was evaluated in the same manner as in Example 11, with the exception that hydrogenolysis of butylbutyrate was performed under conditions of a reaction temperature of 175° C. and a space velocity of 1.0 $h^{-1}$. After 324 hours, the catalyst was recycled using nitrogen gas containing 5% oxygen at 250° C. and then reduced using nitrogen gas containing 5% hydrogen at 200° C., and thus the durability of the catalyst for up to 720 hours was measured. The results are summarized in Table 13 below. The yield of butylbutyrate was decreased from the initial 92% to 82% after 324 hours. After having been recycled using oxygen, the catalyst was restored to its initial activity, and the degree of inactivation of the catalyst was slower than before recycling of the catalyst. Hence, even after 720 hours, a yield of about 86% could be maintained. Accordingly, even if the catalyst was inactivated to some degree, when it was periodically recycled, extended use thereof was possible.

TABLE 13

Effects of Hydrogen to Butylbutyrate Ratio on Hydrogenolysis

| Reaction Time (hours) | 10 | 100 | 324 | 360 | 480 | 720 |
|---|---|---|---|---|---|---|
| Yield of Butylbutyrate (%) | 92.2 | 86.2 | 82.5 | 93.2 | 88.7 | 86.2 |

EXAMPLE 15

Measurement of Octane and Cetane Numbers of Butanol and Butylbutyrate

Butanol and butylbutyrate were respectively added in amounts of 10 vol % and 20 vol % to general gasoline, after which the octane number was measured, and then the blending octane number was calculated. The results are given in Table 14 below. The blending octane number of butanol was confirmed to be equal to that of butylbutyrate.

TABLE 14

| Mixing Ratio | Measured Octane Number | Blending Octane Number of Butanol or Butylbutyrate |
|---|---|---|
| Gasoline 100% | 92.0 | — |
| Gasoline 90% + Butanol 10% | 92.4 | 96 |
| Gasoline 80% + Butanol 20% | 93.8 | 101 |
| Gasoline 90% + Butylbutyrate 10% | 92.4 | 96 |
| Gasoline 80% + Butylbutyrate 20% | 93.6 | 100 |

Butanol and butylbutyrate were respectively added in amounts of 5% and 10% to general diesel, after which the cetane number was measured, and then the blending cetane number was calculated. The results are given in Table 15 below. Whereas the blending cetane number of butanol was about 0, the blending cetane number of butylbutyrate was about 25~30. For the reference, the blending cetane number of soybean biodiesel was measured to be 40~45.

TABLE 15

| Mixing Ratio | Measured Cetane Number | Blending Cetane Number of Biofuel |
|---|---|---|
| Diesel 100% | 55.55 | — |
| Diesel 95% + Butanol 5% | 52.96 | 3.75 |
| Diesel 90% + Butanol 10% | 49.97 | −0.25 |
| Diesel 95% + Butylbutyrate 5% | 54.24 | 29.35 |
| Diesel 90% + Butylbutyrate 10% | 52.50 | 25.05 |
| Diesel 95% + Soybean Biodiesel 5% | 55.02 | 44.9 |
| Diesel 90% + Soybean Biodiesel 10% | 54.20 | 41.9 |

As described hereinbefore, the present invention provides a method of extracting butyric acid from a broth and chemically converting butyric acid into biofuel. According to the present invention, extraction of butyric acid and chemical conversion thereof into butanol can be effectively combined, and thus, biobutanol which is next-generation biofuel can be efficiently and economically produced. Further, butylbutyrate, which has oxidation stability superior to that of conventional biodiesel (fatty acid methyl ester) and is thus regarded as novel biofuel, can be produced together.

Although the embodiments of the present invention have been disclosed for illustrative purposes, those skilled in the art will appreciate that various modifications, additions and substitutions are possible, without departing from the scope and spirit of the invention as disclosed in the accompanying claims.

The invention claimed is:

1. A method of producing a biofuel from fermented butyric acid, comprising:
   a) providing a fermentation broth containing butyric acid produced through fermentation of a carbohydrate;
   b) subjecting the fermentation broth to extraction in a liquid-liquid extraction column using trialkylamine as an extraction solvent to obtain the butyric acid in the form of trialkylammonium butyrate;
   c) supplying the trialkylammonium butyrate to a distillation column to separate the trialkylammonium butyrate into butyric acid and trialkylamine; and
   d) converting the butyric acid separated from the distillation column into butylbutyrate through esterification with butanol, and supplying the trialkylamine separated from the distillation column to the liquid-liquid extraction column as the extraction solvent for step b).

2. The method as set forth in claim 1, wherein the trialkylamine is selected from the group consisting of tripentylamine, trihexylamine, trioctylamine and tridecylamine.

3. The method as set forth in claim 1, wherein the esterification of the butyric acid is performed under reaction conditions including a reaction temperature of 80~300° C., a reaction pressure ranging from atmospheric pressure to 20 atm, a space velocity of 0.1~5.0 h$^{-1}$ and a molar ratio of butanol to butyric acid of 1~10, in presence of at least one catalyst having an esterification function.

4. The method as set forth in claim 1, wherein the esterification of the butyric acid is performed under reaction conditions including a reaction temperature of 90~200° C., the reaction pressure ranging from atmospheric pressure to 10 atm, a space velocity of 0.3~2.0 h$^{-1}$ and a the molar ratio of butanol to butyric acid of 1.5~5.

5. The method as set forth in claim 1, wherein a catalyst used for the esterification of the butyric acid is a homogeneous catalyst or a heterogeneous catalyst, in which the homogeneous catalyst comprises sulfuric acid, hydrochloric acid or nitric acid, and the heterogeneous catalyst is selected from the group consisting of solid acid catalysts having super strong acid properties, including an ion exchange resin, zeolite, silica alumina, alumina, sulfonated carbon and heteropolyacid.

6. The method as set forth in claim 1, wherein the biofuels are butanol, butylbutyrate or a mixture of butanol and butylbutyrate.

7. The method as set forth in claim 1, wherein the fermentation is performed by continuously adding an aqueous carbohydrate solution to a fermentation reactor packed with a support on which a strain for producing butyric acid is immobilized so that the carbohydrate in the aqueous carbohydrate solution is fermented into butyric acid.

8. The method as set forth in claim 7, wherein the strain for producing butyric acid is *Clostridium tyrobutylicum*, *Clostridium butylicum* or *Clostridium acetobutyricum*.

9. The method as set forth in claim 1, further comprising: e) converting the butylbutyrate into butanol through hydrogenolysis with hydrogen.

10. The method as set forth in claim 9, wherein a part of the butanol converted in step e) is recycled to step d) for the esterification of the butyric acid.

11. The method as set forth in claim 10, wherein the other part of the butanol converted in step e) is recovered as a final product.

12. The method as set forth in claim 9, wherein a biogas discharged through the fermentation is supplied to a pressure swing adsorption unit so that the biogas is separated into hydrogen and carbon dioxide, and the separated hydrogen is used for the hydrogenolysis in step e).

13. The method as set forth in claim 9, wherein the hydrogenolysis is performed under reaction conditions including a reaction temperature of 120~300° C., a reaction pressure ranging from atmospheric pressure to 100 atm, a space velocity of 0.1~5.0 h$^{-1}$ and a molar ratio of hydrogen to butylbutyrate of 1~100, in presence of a catalyst having a hydrogenation function in a form in which at least one metal or metal oxide is supported on a support.

14. The method as set forth in claim 13, wherein the at least one metal or metal oxide is selected from the group consisting of copper, zinc, chromium, nickel, cobalt, molybdenum, tungsten, oxides thereof, platinum, palladium, ruthenium, rubidium and oxides thereof.

15. The method as set forth in claim 9, wherein the hydrogenolysis is performed under reaction conditions including a reaction temperature of 150~250° C., a the reaction pressure of 5~50 atm, a space velocity of 0.3~2.0 h$^{-1}$ and a the molar ratio of hydrogen to butylbutyrate of 10~50.

* * * * *